US00PP19974P3

(12) United States Plant Patent

Brown et al.

(10) Patent No.: US PP19,974 P3

(45) Date of Patent: May 5, 2009

(54) HYBRID BERMUDAGRASS PLANT NAMED 'EMERALD DWARF'

(50) Latin Name: *Cynodon×Cynodon transvaalensis hybrid*
Varietal Denomination: Emerald Dwarf

(75) Inventors: Richard Morris Brown, Bay City, TX (US); Michael Andrew Brown, Bay City, TX (US); Scott Derek Brown, Bay City, TX (US)

(73) Assignee: Coastal Turf, Inc., Bay City, TX (US)

( * ) Notice: Subject to any disclaimer, the term of this patent is extended or adjusted under 35 U.S.C. 154(b) by 86 days.

(21) Appl. No.: 11/796,317

(22) Filed: Apr. 27, 2007

(65) Prior Publication Data

US 2008/0271218 P1 Oct. 30, 2008

(51) Int. Cl.
*A01H 5/00* (2006.01)

(52) U.S. Cl. ..... Plt./389

(58) Field of Classification Search ..... Plt./389
See application file for complete search history.

(56) References Cited

U.S. PATENT DOCUMENTS

| | | | |
|---|---|---|---|
| PP9,030 | P | 1/1995 | Dudeck |
| PP9,888 | P | 5/1997 | Brown et al. |
| PP10,079 | P | 10/1997 | Hanna |
| PP10,332 | P | 4/1998 | Krans et al. |
| PP11,163 | P | 12/1999 | Hanna |
| PP12,084 | P2 | 9/2001 | Kaerwer et al. |
| PP13,178 | P2 | 11/2002 | Doguet |

OTHER PUBLICATIONS

Gibeault, V.A., S. T. Cockerham, S.B. Ries, and R. Autio, Coachella Valley Turfgrass Research Project, Oct. 2003, University of California, Riverside.

*Primary Examiner*—Annette H Para
(74) *Attorney, Agent, or Firm*—Akin Gump Strauss Hauer & Feld LLP

(57) ABSTRACT

A hybrid Bermudagrass cultivar, named 'Emerald Dwarf,' is distinguished by greater rhizome development and rooting depth in conjunction with low surface stolon development. The cultivar is especially suited to golf greens.

20 Drawing Sheets

Latin name of the genus and species of the plant claimed: *Cynodon dactylon×Cynodon transvaalensis hybrid.*
Variety denomination: 'Emerald Dwarf' Bermudagrass.

BACKGROUND OF THE INVENTION

The present invention relates to a new and distinct Bermudagrass plant. Bermudagrass (*Cynodon* spp. L. C. Rich) is one of the most important and widely used warm-season turfgrasses. It is adapted to the warm- and subtropical-climatic regions of the world. The turf-type Bermudagrasses are $C_4$, perennials that originated in southeastern Africa. The common turf-type species of *Cynodon* include: *Cynodon dactylon* (L.) Pers. or *dactylon* Bermudagrass which is a tetraploid; and *Cynodon transvaalensis* (Burtt-Davy) or African Bermudagrass which is a diploid. The *dactylon* Bermudagrasses as a group are characterized by a relatively coarse leaf width and lower shoot density, while the hybrid bermudagrasses tend to have narrower leaf width and higher shoot density. Both are relatively low-growing via vigorous lateral stems, both rhizomes and stolons.

Putting greens in the warm, humid climatic regions of the United States are usually planted with Bermudagrass. Once, two Bermudagrass varieties dominated use on putting greens: 'Tifgreen (328),' released in 1956 and 'Tifdwarf,' released in 1965, but with the introduction of 'Champion' in the late 1990s, the group of grasses often referred to collectively as Ultradwarf Bermudagrasses have been the most widely used on greens for the last 10 years. These grasses include 'Champion' (PP 9,888), 'Floradwarf' (PP 9,030), 'Mississippi Supreme' (PP 11,781), 'Tifeagle' (PP 11,163), and 'Minverde' (PP 12,084).

There are six basic components of turfgrass quality: (a) uniformity, (b) density, (c) texture, (d) growth habit, (e) smoothness, and (f) color.

The expectations of today's golfers for fast, smooth putting greens have resulted in heights of cut which are significantly lower than they were in the past. A height of cut of ⅛" was unheard of prior to the late 1980's, yet it is now commonplace. A modern putting green cultivar must be able to withstand this height of cut in order to be successful. While the Ultradwarf Bermudagrasses as a group do tolerate low greens heights, experience has shown that they can present unique challenges for the golf course manager because of their growth habit. The aspects of these grasses' growth habit which are problematic include: very high shoot density, lateral growth which is comprised almost entirely of stolons, and, shallow rooting, as shown by Table 1 below.

TABLE 1

Shoots, roots, stolons, and rhizomes for five Bermudagrasses*

| Cultivar | Shoots (No. in$^2$) | Roots (mg) | Stolons (mg) | Rhizomes (mg) |
|---|---|---|---|---|
| 'Champion' | 119 a | 230 a | 910 | 4 b |
| 'Floradwarf' | 80 bc | 130 bc | 780 | 0 b |
| 'Miniverde' | 120 a | 220 a | 870 | 16 b |

TABLE 1-continued

| Cultivar | Shoots, roots, stolons, and rhizomes for five Bermudagrasses* | | | |
|---|---|---|---|---|
| | Shoots (No. in$^2$) | Roots (mg) | Stolons (mg) | Rhizomes (mg) |
| 'Tifeagle' | 92 b | 100 c | 730 | 18 b |
| 'Tifdwarf' | 66 c | 270 a | 780 | 200 a |

*planted 15 Apr. 1997 at the Texas A&M University Turfgrass Field Laboratory in College Station, TX and sampled Aug. 26, 1997

Some of the problems which have been associated with this growth habit include scalping, difficulty in moving water into the rootzone causing turf loss due to desiccation, severe disease outbreaks, difficulty in establishing and transitioning from overseeding, thatch accumulation, severe "grain" or "stem displaysia", and lack of recuperative potential. Many courses have replaced some of these Ultradwarf varieties with other grasses after having significant difficulties managing them.

While it is important for a turfgrass selected for putting greens to possess the ability to withstand low greens heights, there has been a pronounced desire among golf course superintendents to have a cultivar with a growth habit which would allow it to tolerate low heights of cut while still responding to management practices which were successful on the older varieties 'Tifdwarf' and 'Tifgreen (328).'

BRIEF SUMMARY OF THE INVENTION

'Emerald Dwarf' Bermudagrass is a dwarf triploid hybrid Bermudagrass (*Cynodon dactylon*×*Cynodon transvaalensis*) that has the extraordinary morphological characteristics of substantially greater rhizome development when compared in replicated studies with the closest known cultivars of *Cynodon* spp. It also possesses a significantly greater rooting depth and root mass by depth under putting greens maintenance. This grown habit allows it to tolerate very low heights of cut, yet it does so without the management difficulties that have been associated with ultradwarf Bermudagrasses. In addition, in comparison to ultradwarf bermudagrasses, 'Emerald Dwarf' has higher overseeding color and quality, better uniformity during transition of overseeded putting greens grasses, and higher percentage coverage of Bermudagrass during that transition. All of these characteristics make it an excellent quality surface for putting greens, bowling greens, cricket wickets, croquet courts, and lawn tennis courts.

BRIEF DESCRIPTION OF THE PHOTOGRAPHS

DETAILED BOTANICAL DESCRIPTION

Origin of the Cultivar

Figure 1:
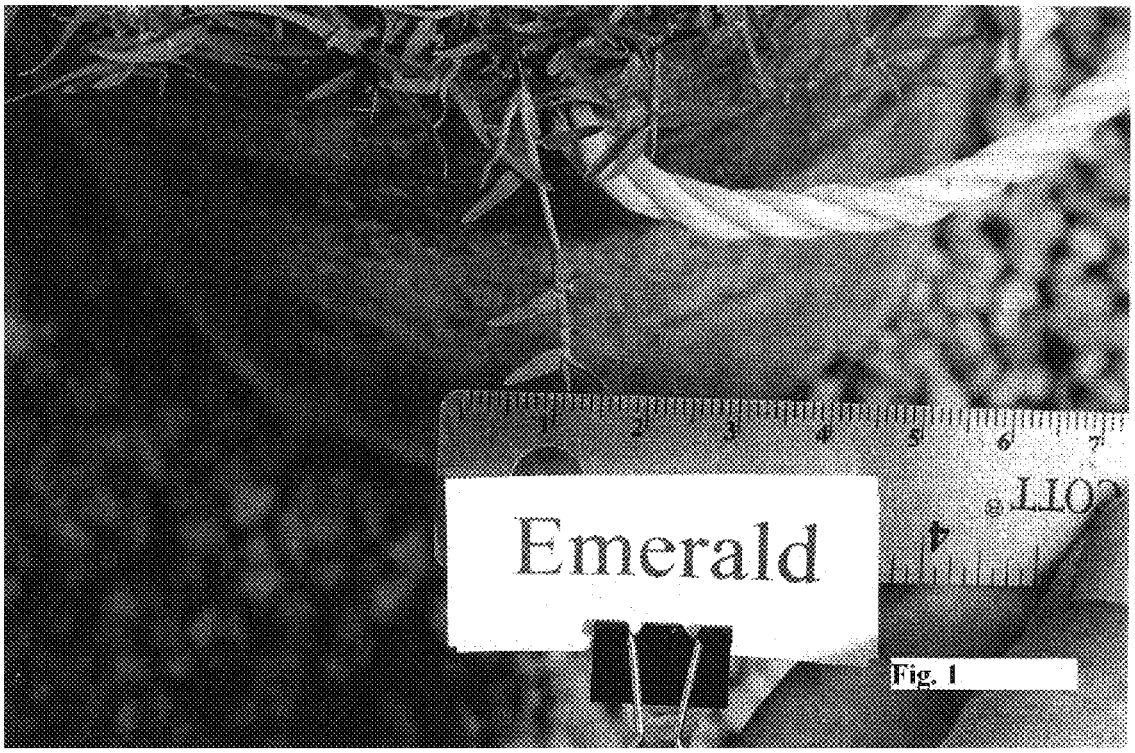
FIGS. 1–3 are close-up photographs of 'Emerald Dwarf', 'Tifdwarf,' and 'Tifeagle' showing leaf morphology.
Figure 2:
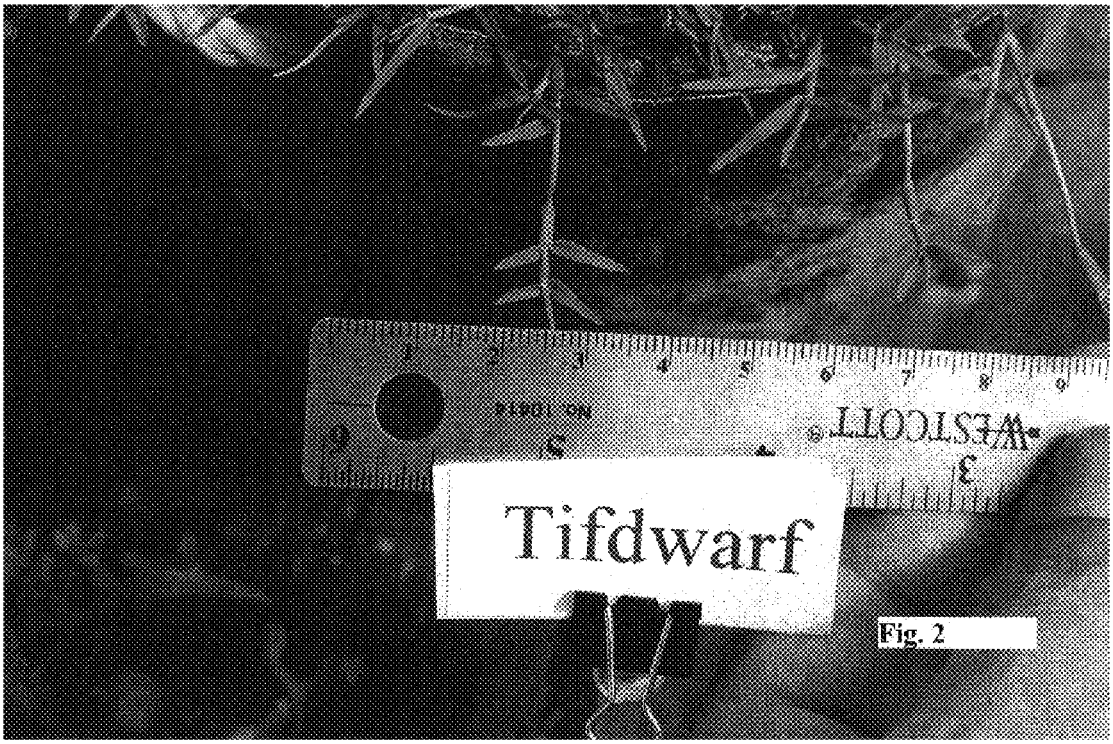
Figure 3:
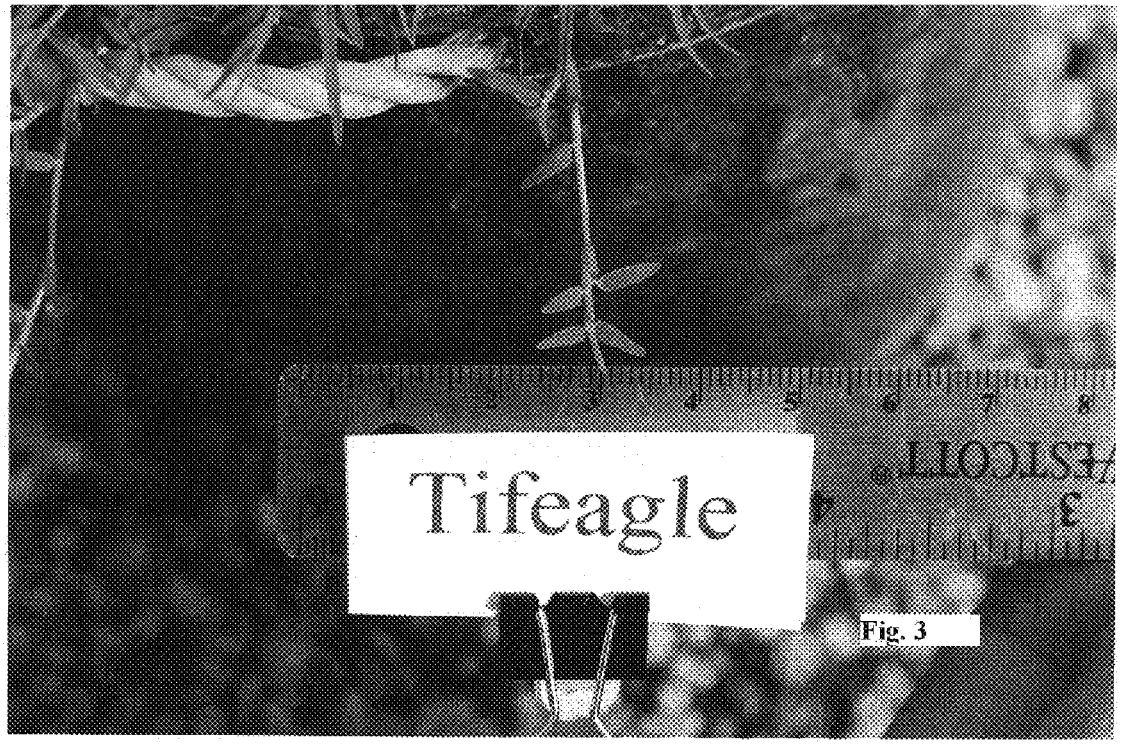

The genotype 'Emerald Dwarf' is new and distinct natural turfgrass selection from a segregated patch found on a putting green in Houston in 1992. The putting green had been originally planted with 'Tifdwarf' hybrid Bermudagrass (*Cynodon dactylon*×*Cynodon transvaalensis*) in the early 1970s. The grass was propagated from a single sprig in one-gallon pots at patentees Bay City, Tex. facility. It was then further cut into individual sprigs and planted in trays, and a 20,000 sq. ft. area was then planted in trays. This was then propagated into a 1.2 acre growth area. A short lateral stem with a single node was used for asexual vegetative propagation and increase of the original source of 'Emerald Dwarf'.

Taxonomy

'Emerald Dwarf' is a triploid, hybrid Bermudagrass (*Cynodon dactylon*×*Cynodon transvaalensis*).

Morphological Characterization

Compared to other Bermudagrass cultivars, 'Emerald Dwarf' has the advantageous morphological characteristics of high rhizome production and relatively high rooting depth and mass, in conjunction with low surface stolon development. In addition, 'Emerald Dwarf' has improved overseeding color and quality, greater uniformity during transition periods, and greater coverage of Bermudagrass during transition over other ultradwarf Bermudagrasses. Applicants choose to describe the color characteristics of the 'Emerald Dwarf' with reference to the Royal Horticultural Society's color numbering system ("R.H.S. Color Chart").

Compared to 'Tifgreen 328,' 'Emerald Dwarf' has greater shoot density, greater rhizome development, darker green color described by the R.H.S. Color Chart as R.H.S. 138A, medium light green, smaller leaf morphology, tighter internode length, and fewer seed heads.

Compared to 'Tifdwarf,' 'Emerald Dwarf' has similar shoot density, leaf morphology, and seedhead production, but has substantially greater rhizome development, a substantially greater ratio of rhizomes to stolons, and significantly deeper rooting depth. Unlike 'Tifdwarf,' 'Emerald Dwarf' does not exhibit short day-length senescences (opening canopy in fall), and does not form a thick mat of stolons near the surface.

Compared to ultradwarf Bermudagrasses, 'Emerald Dwarf' has a lower shoot density, substantially greater rhizome development, substantially greater root mass and diameter, less thatch production, substantially greater rooting depth, and is much more tolerant of heavy vertical moving. 'Emerald Dwarf' has fewer and larger lateral stems than ultradwarf Bermudagrasses. Unlike ultradwarf Bermudagrasses, 'Emerald Dwarf' does not form a thick mat of stolons near the surface, naturally forms a firm surface which is not prone to scalping, and does not form grain or "sheen." 'Emerald Dwarf' does not substantially restrict water infiltration into the rootzone, allowing for infrequent, deep watering cycles.

This new and distinct combination of morphological characteristics has been retained through succeeding multiple generations of asexual vegetative propagation. These traits render 'Emerald Dwarf' particularly suitable for golf greens.

Leaf Blade Width

Quantitative assessments of leaf blade widths revealed 'Emerald Dwarf' to have a mid-range leaf blade width and allied fine turf canopy texture. The leaf blade width of 'Emerald Dwarf' was found to be significantly more fine than two hybrid Bermudagrass cultivars, being 13.3% less than 'Tifgreen' and 8.2% less than 'Tifdwarf' (see Table 2), and significantly less fine than one hybrid Bermudagrass cultivar, being 18.1% more than 'Tifeagle.'

TABLE 2

Leaf Blade Width* Comparisons Among Four Bermudagrass (*Cynodon* spp.) Genotypes

| Genotypes | Leaf Blade Width (mm) |
|---|---|
| 'Emerald Dwarf' | 1.3 |
| 'Tifgreen (328)' | 1.5 |
| 'Tifdwarf' | 1.4 |
| 'Tifeagle' | 1.1 |

*Measured at the midpoint length of the youngest, fully expanded leaf blade on a shoot, with six blade measurements per replicate container.

Leaf Blade Length

Figure 19:
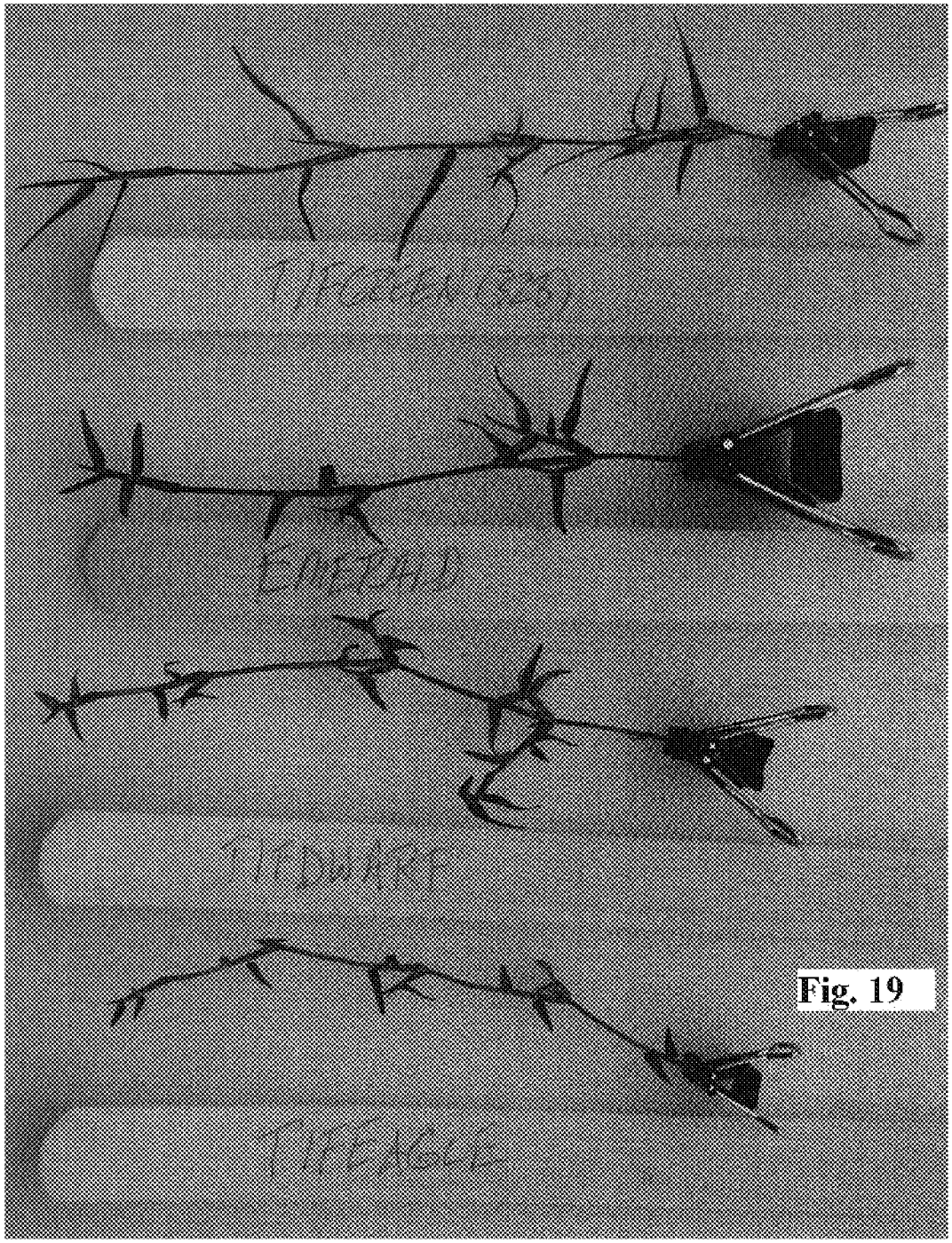
FIG. 19 is a close-up photograph of 'Emerald Dwarf,' 'Tifdwarf,' and 'Tifeagle' showing relative leaf lengths.

Quantitative assessments of leaf blade lengths revealed 'Emerald Dwarf' to have a mid-range leaf blade length. The leaf blade length of 'Emerald Dwarf' was found to be significantly longer than two hybrid Bermudagrass cultivars, being 46.4% more than 'Tifeagle' and 10.8% more than 'Tifdwarf' (see Table 3) and significantly shorter than another hybrid Bermudagrass cultivar, being 37.9% less than 'Tifgreen (328).' FIG. 19 is a photograph showing a comparison of the leaf lengths of 'Emerald Dwarf,' 'Tifgreen (328),' 'Tifdwarf,' and 'Tifeagle.'

TABLE 3

Leaf Blade Length* Comparisons Among Four Bermudagrass (*Cynodon* spp.) Genotypes

| Genotypes | Leaf Blade Length (mm) |
|---|---|
| 'Emerald Dwarf' | 16.4 |
| 'Tifgreen (328)' | 26.4 |
| 'Tifdwarf' | 14.8 |
| 'Tifeagle | 11.2 |

*Measured on the third leaf from the end of the stolon, with six blade measurements per replicate container.

Internode Length

Figure 4:
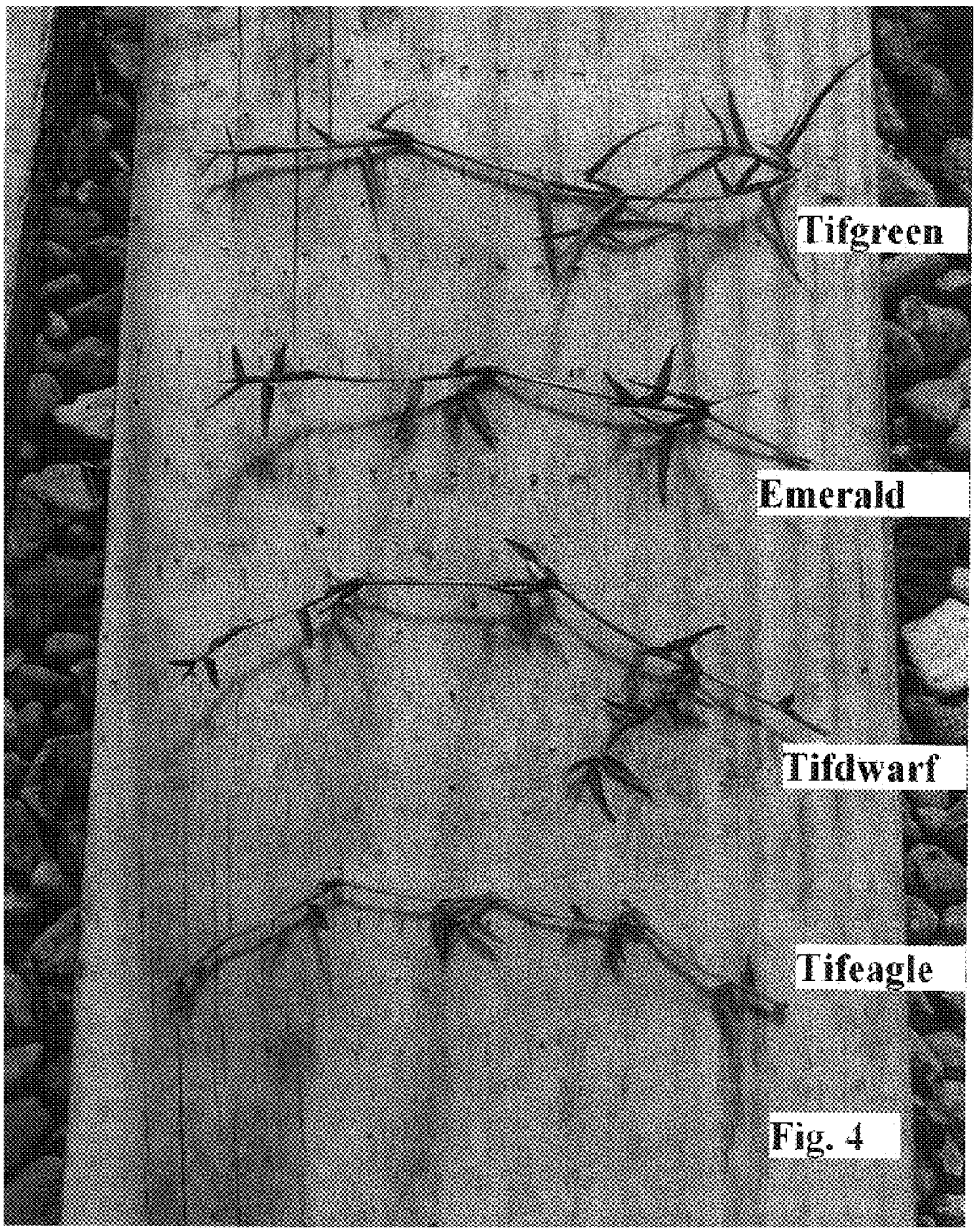
FIG. 4 is a photograph illustrating the comparative internode length of 'Emerald Dwarf,' 'Tifgreen (328),' 'Tifdwarf,' and 'Tifeagle'.

Quantitative assessments of internode lengths revealed 'Emerald Dwarf' to have a mid-range internode length. The internode length of 'Emerald Dwarf' was found to be significantly longer than two hybrid Bermudagrass cultivars, being 9% more than 'Tifdwarf' and 40.4% more than 'Tifeagle' (see Table 4) and significantly shorter than another hybrid Bermudagrass cultivar, being 65.8% less than 'Tifgreen (328).' FIG. 4 illustrates the comparative internode length of 'Emerald Dwarf,' 'Tifgreen (328),' 'Tifdwarf,' and 'Tifeagle.'

TABLE 4

Internode Length* Comparisons Among Four Bermudagrass (*Cynodon* spp.) Genotypes

| Genotypes | Internode Length (mm) |
|---|---|
| 'Emerald Dwarf' | 14.6 |
| 'Tifgreen (328)' | 22.2 |
| 'Tifdwarf' | 13.4 |
| 'Tifeagle' | 10.4 |

*Measured between the third and fourth node from the terminal end of the stolon, with six blade measurements per replicate container.

Rhizomes vs. Stolons After 18 Months

Figure 5:
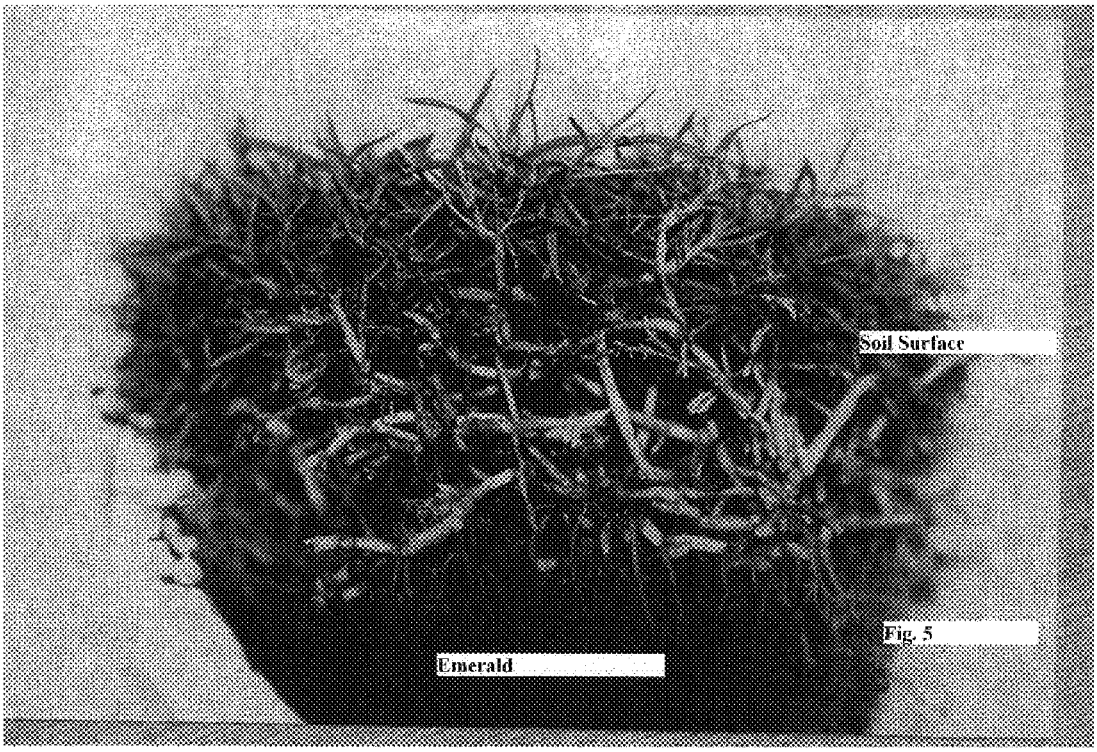
FIG. 5 is a close-up photograph of 'Emerald Dwarf' showing rhizome formation in native clay soil.
Figure 6:
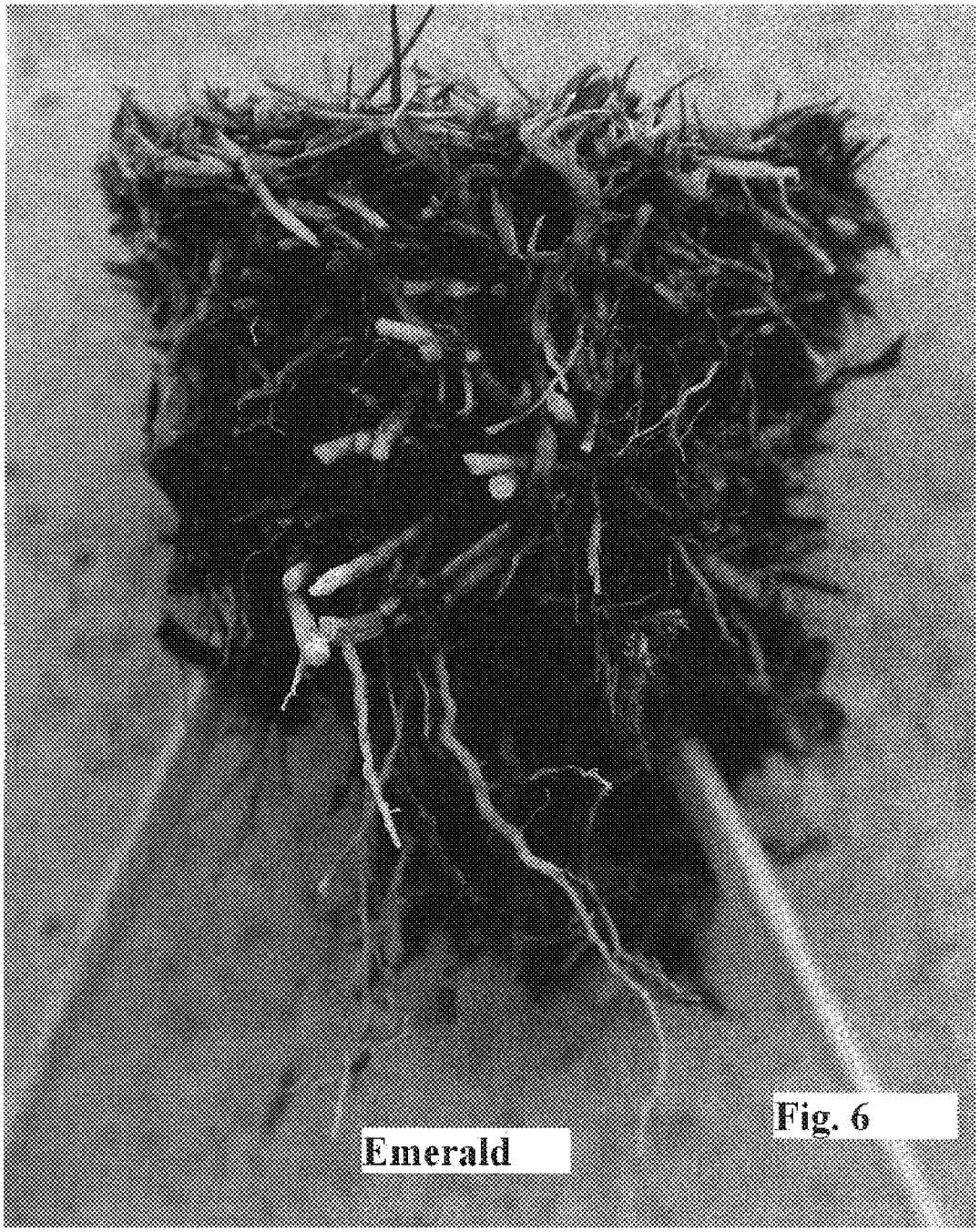
FIGS. 6–9 are close-up photographs of 'Emerald Dwarf,' 'Tifdwarf,' 'Tifgreen (328),' and 'Tifeagle,' showing relative rhizome and stolon formation.
Figure 7:
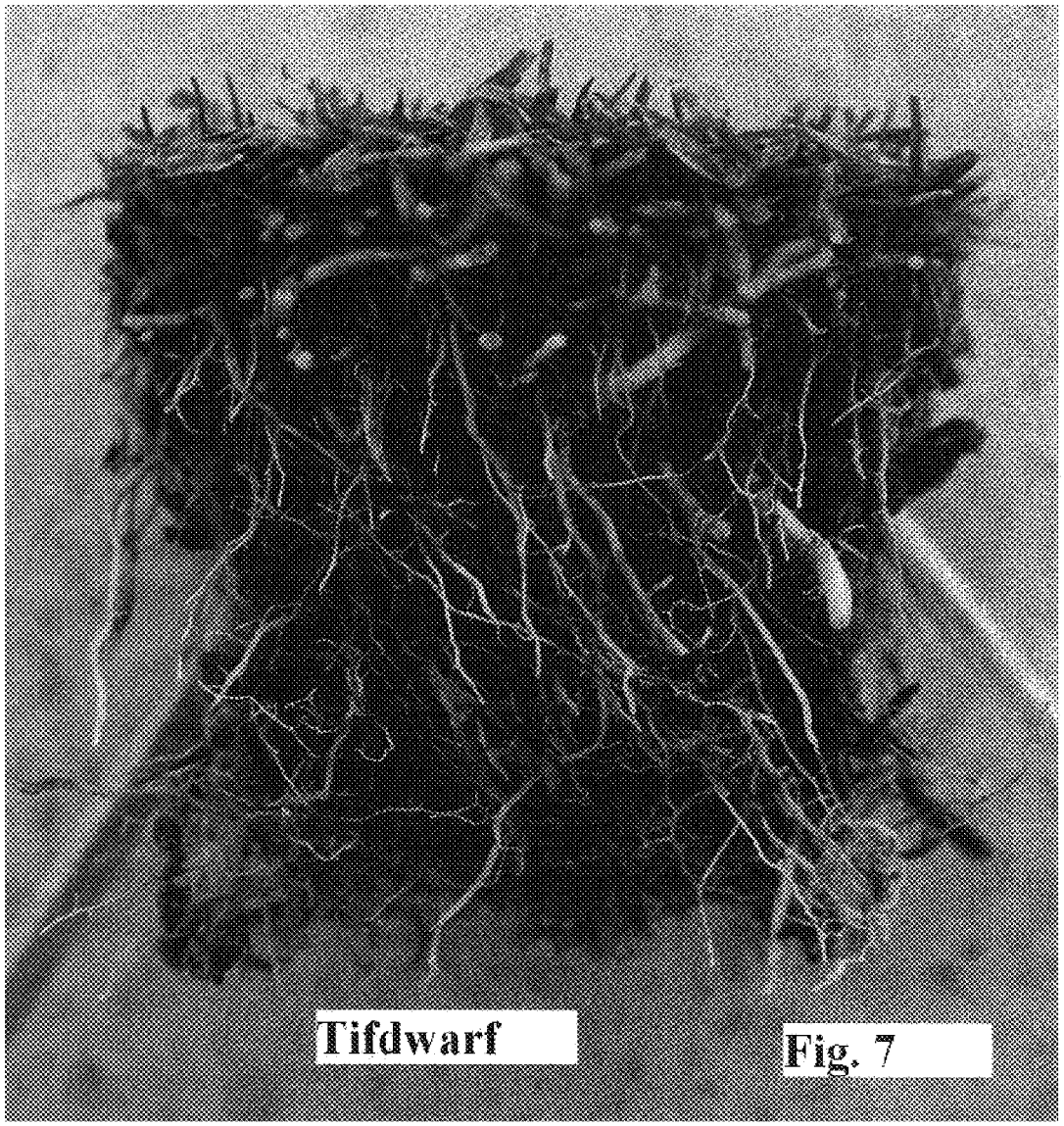
Figure 8:
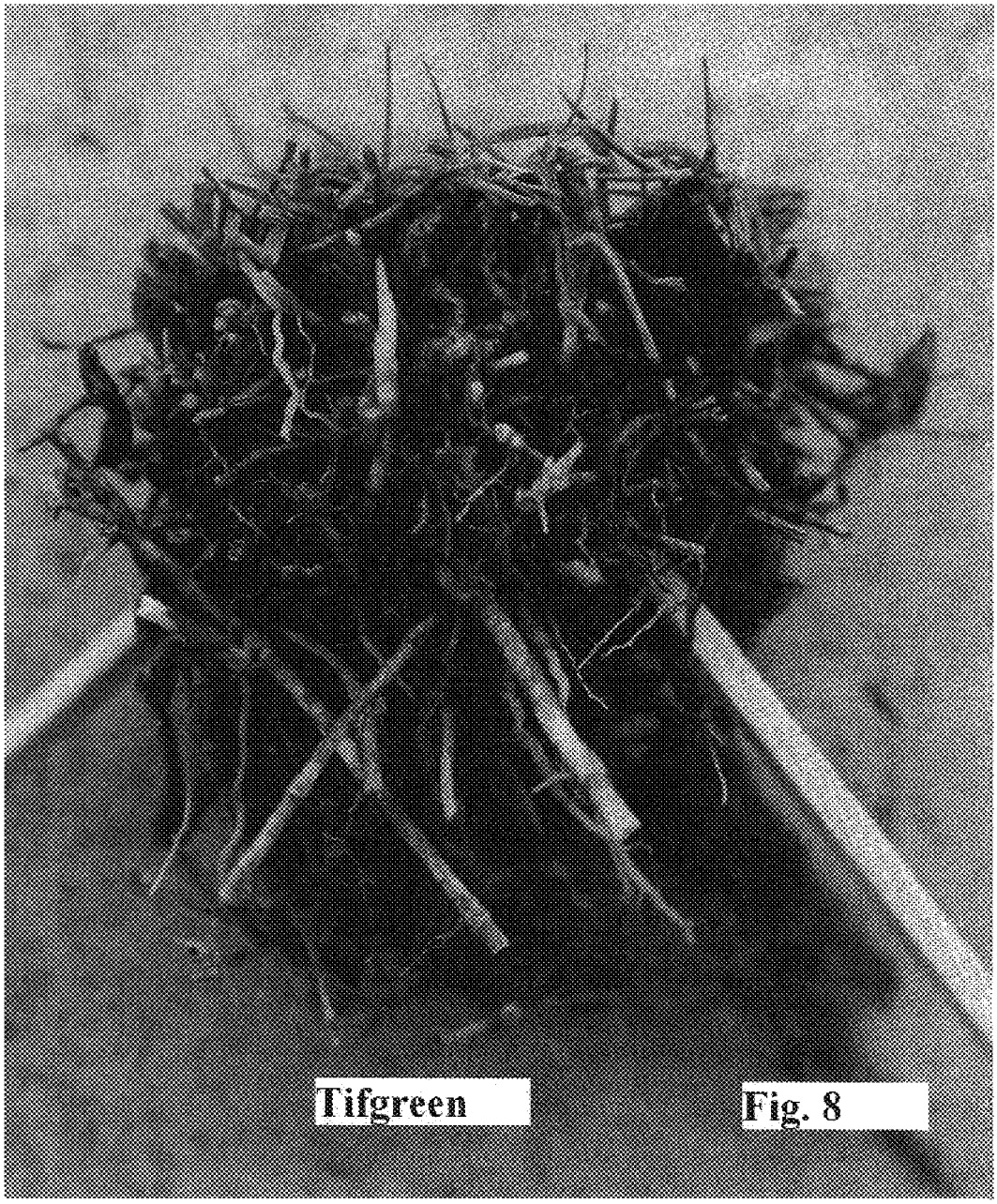
Figure 9:
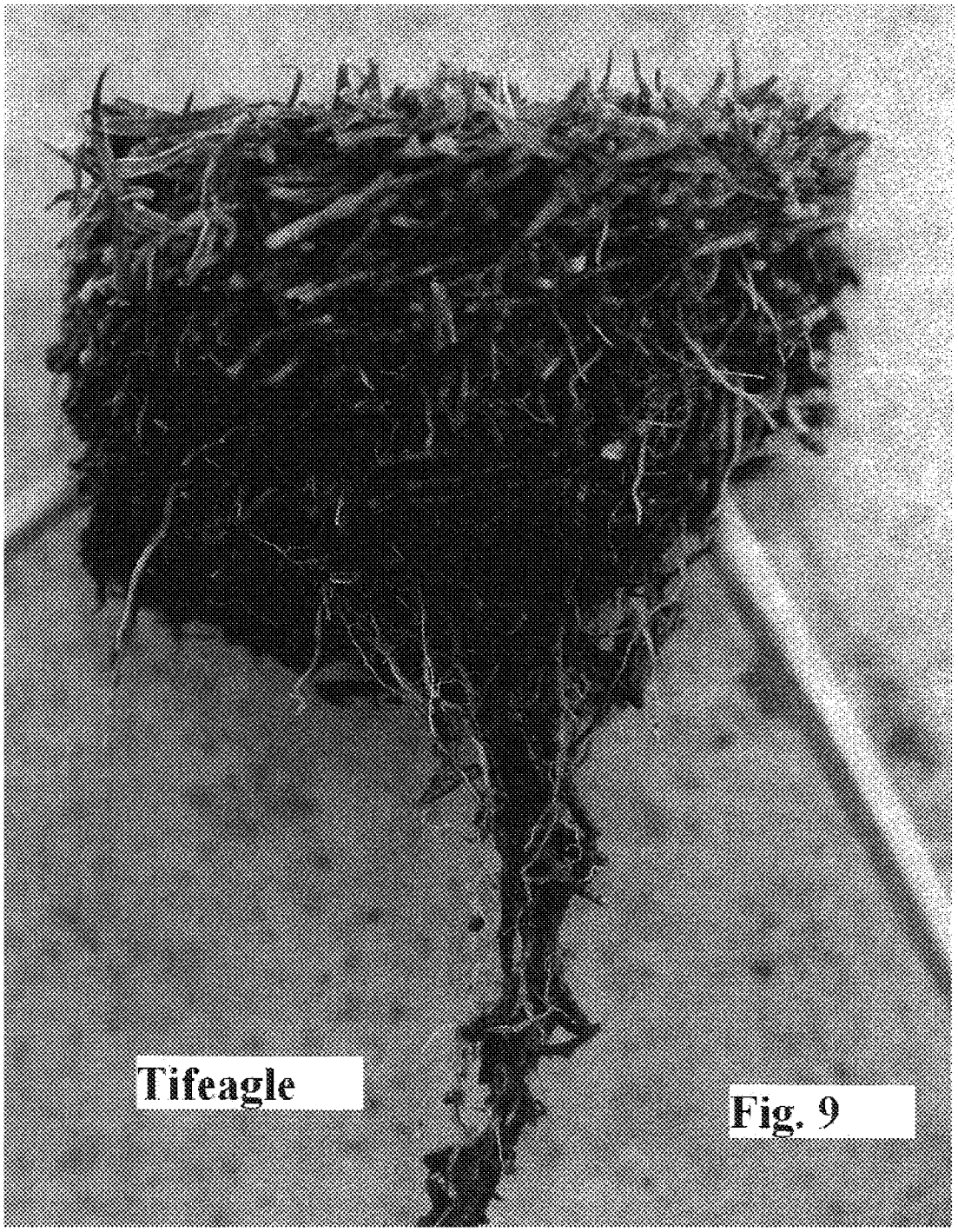

Quantitative assessments of the number of rhizomes and stolons under putting greens maintenance after 18 months revealed 'Emerald Dwarf' to have a comparatively high rhizome to stolon ratio. The rhizome percentage of 'Emerald Dwarf' was found to be significantly higher than three hybrid Bermudagrass cultivars, being 71.4% higher than 'Tifgreen (328),' 200% higher than 'Tifdwarf,' and 1100% higher than 'Tifeagle' (see Table 5). FIG. 5 illustrates the rhizome formation of 'Emerald Dwarf' in native clay soil. FIGS. 6–9 illustrate the comparative formation of relative rhizome and stolon formation of 'Emerald Dwarf,' 'Tifgreen (328),' 'Tifdwarf,' and 'Tifeagle' after 18 months of growth at putting greens height (0.125"–0.187").

TABLE 5

Rhizomes vs. Stolons After 18 Months* Comparisons Among Four Bermudagrass (*Cynodon* spp.) Genotypes

| Genotypes | % Rhizomes | % Stolons |
|---|---|---|
| 'Emerald Dwarf' | 60 | 40 |
| 'Tifgreen (328)' | 35 | 65 |
| 'Tifdwarf' | 20 | 80 |
| 'Tifeagle' | 5 | 95 |

*Orientation of lateral stem growth in profiles removed from replicate plots maintained under putting greens maintenance, with samples taken 18 months after planting. HOC was 0.125 April-October, 0.157 November-March. Means of four replications assessed November 2000.

Shoot Density

Figure 10:
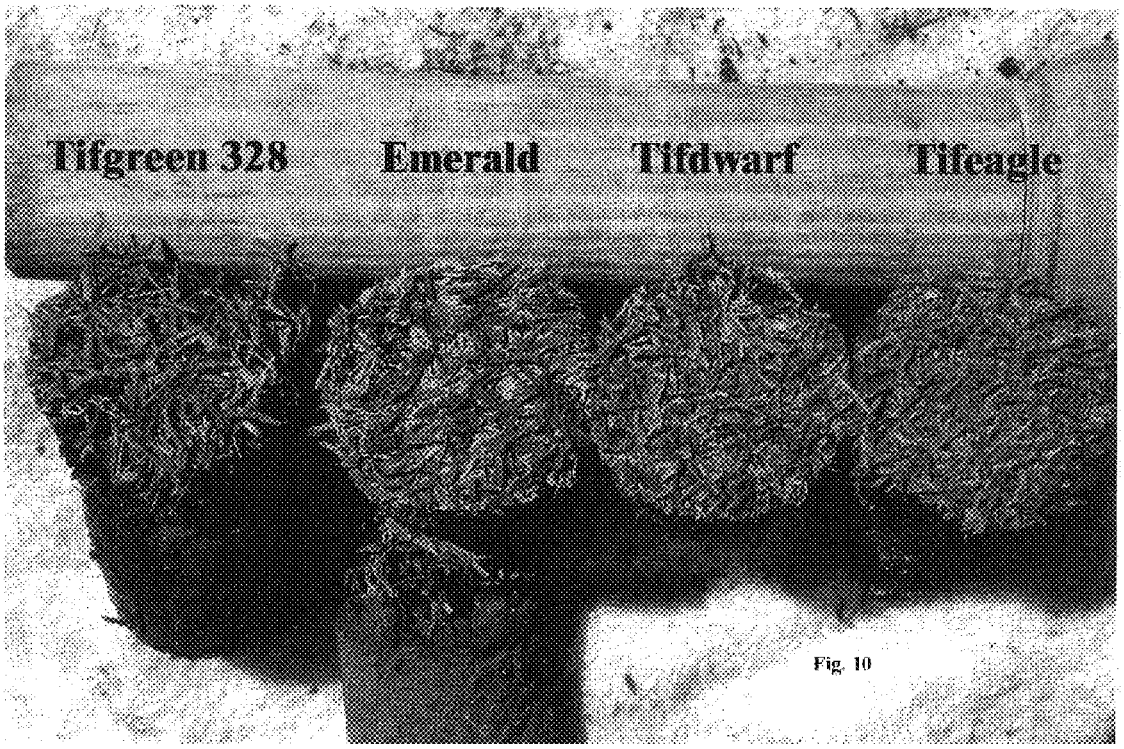
FIG. 10 is a close-up photograph of comparative plugs of 'Emerald Dwarf,' 'Tifgreen' (328), 'Tifdwarf,' and 'Tifeagle,' take 18 months after planting.

The shoots with leaves originate from the nodes along the lateral stems, from both stolons and rhizomes. A detailed, quantitative assessment was made of the shoot density. A particular concern for Bermudagrass greens is maintaining adequate shoot density at increasingly lower heights. With the improvements in equipment and increasing sophistication of golfers, it is now common to find greens regularly mowed at ⅛". At this height adequate shoot density becomes critical to prevent sunlight from reaching the surface of the soil which will cause algae to grow on the surface. When shoot density is not adequate, weed invasion also becomes more of problem. A concern with the Ultradwarf Bermudagrasses is that these cultivars have such high shoot densities that they required extensive cultivation to perform well long term. This extensive cultivation has been difficult for many superintendents to accomplish because it involves repeated disruption of play. 'Emerald Dwarf' has been found to have a shoot density which is high but not excessive after 18 months, with a 50% greater density than 'Tifgreen (328),' 4.3% greater density than 'Tidwarf,' and 25% lower density than 'Tifeagle.' This is shown by Table 6A below. FIG. 10 illustrates comparative plugs of the four cultivars.

TABLE 6A

Shoot Density After 18 Months* Comparisons Among Four Bermudagrass (*Cynodon* spp.) Genotypes

| Genotypes | Shoot Density (per in$^2$) |
|---|---|
| 'Emerald Dwarf' | 96 |
| 'Tifgreen (328)' | 64 |
| 'Tifdwarf' | 92 |
| 'Tifeagle' | 128 |

*Number of shoots per in$^2$ in samples removed from replicate plots maintained under putting greens maintenance, with samples taken 18 months after planting. HOC was 0.125 April-October, 0.157 November-March. Means of four replications assessed November 2000.

Figure 11:
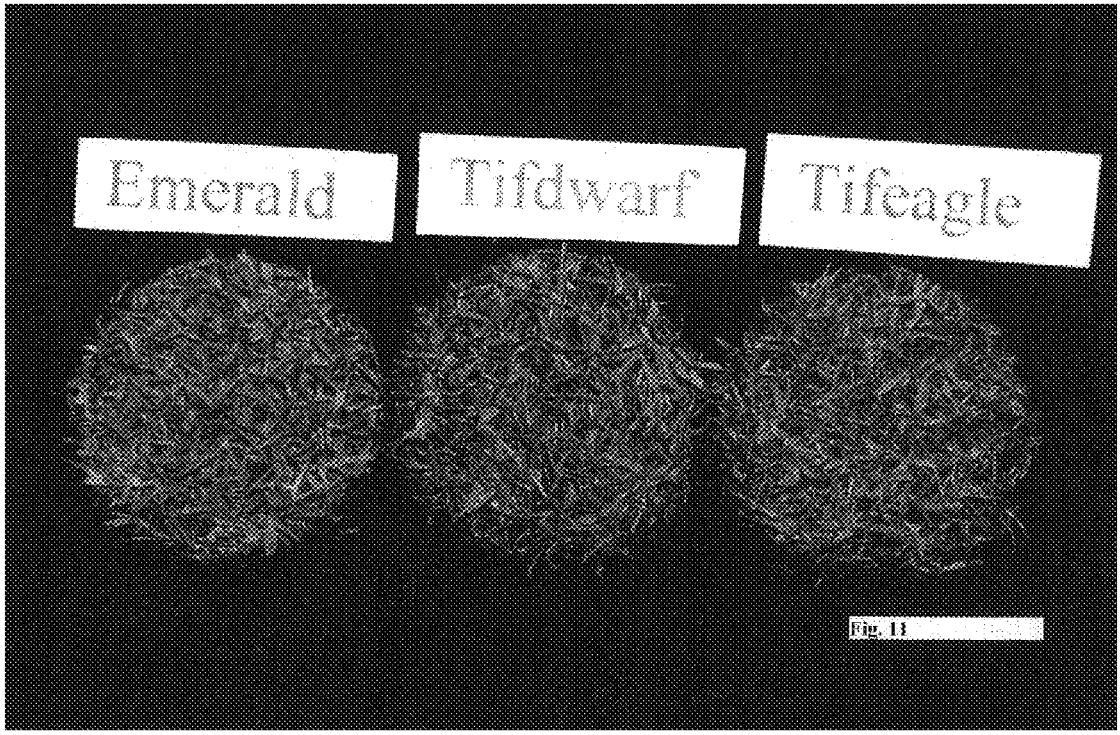
FIG. 11 is a close-up photograph of comparative plugs of 'Emerald Dwarf,' 'Tifdwarf,' and 'Tifeagle,' take 30 months after planting.

A second test was done on shoot density 30 months after planting. Again, 'Emerald Dwarf' has been found to have a midrange shoot density after 30 months, with a 7.3% greater density than 'Tifdwarf,' and 21.4% lower density than 'Tifeagle.' This is shown by Table 6B below. FIG. 11 illustrates comparative plugs of 'Emerald Dwarf,' 'Tifdwarf,' and 'Tifeagle.'

TABLE 6B

Shoot Density After 30 Months* Comparisons Among Three Bermudagrass (*Cynodon* spp.) Genotypes

| Genotypes | Shoot Density (per in$^2$) |
|---|---|
| 'Emerald Dwarf' | 88 |
| 'Tifdwarf' | 82 |
| 'Tifeagle' | 112 |

*Number of shoots per in$^2$ in samples removed from replicate plots maintained under putting greens maintenance, with samples taken 30 months after planting. HOC was 0.125 April-October, 0.157 November-March. Means of four replications assessed October 2001.

Rooting Depth

Figure 12:
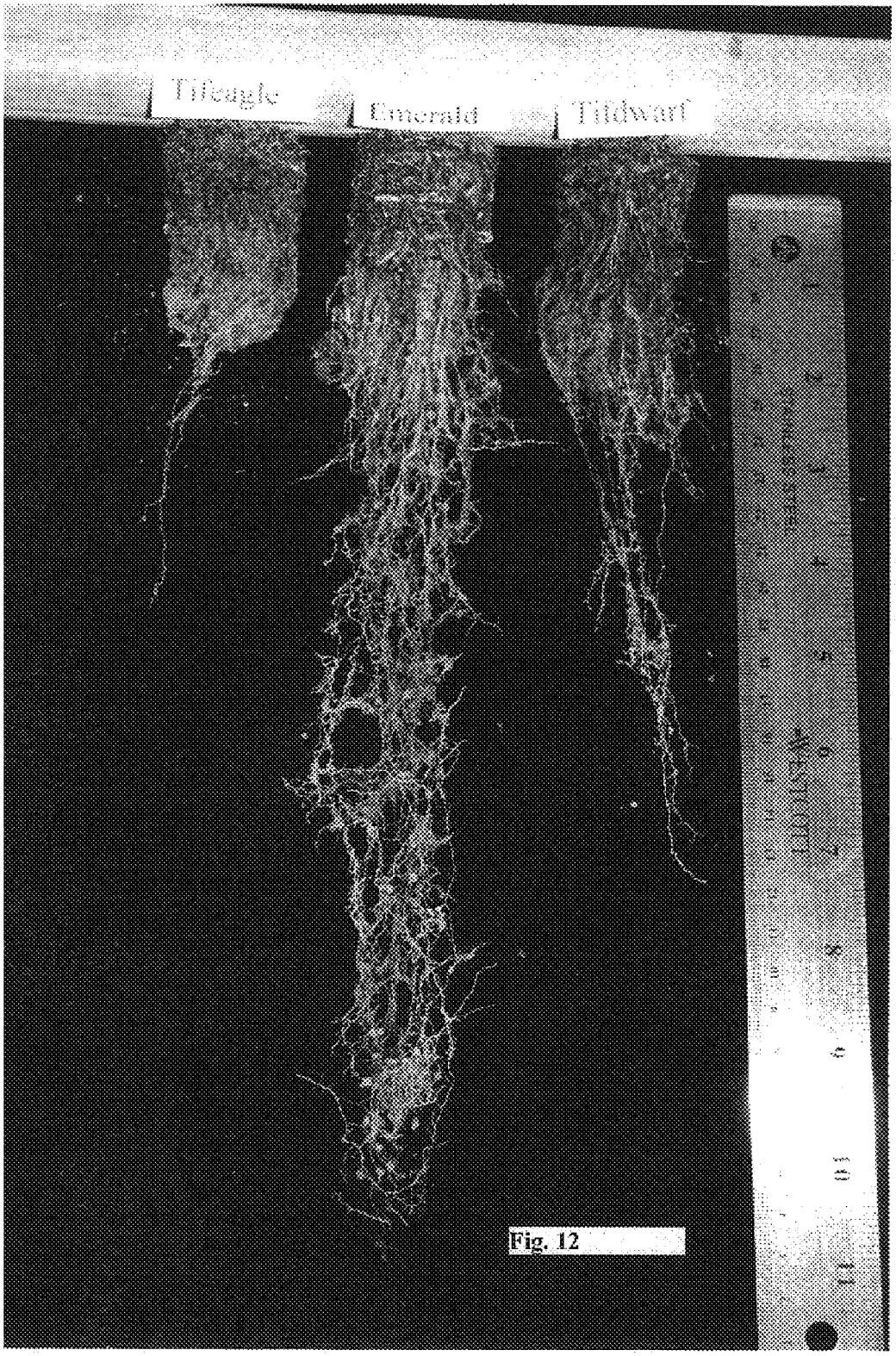
FIG. 12 is a photograph of comparative plugs of 'Emerald Dwarf,' 'Tifeagle,' and 'Tifdwarf,' taken 30 months after planting illustrating comparative root depths.

A detailed, quantitative assessment was made of the rooting depth. 'Emerald Dwarf' has been found to have a comparatively greater root depth after 30 months, with a 49.7% greater depth than 'Tifdwarf,' and 136.9% greater depth than 'Tifeagle.' This is shown by Table 7 below. FIG. 12 illustrates comparative root depths of the three cultivars after 30 months at putting greens height (0.125"–0.187").

TABLE 7

Root Depth After 30 Months* Comparisons Among Three Bermudagrass (*Cynodon* spp.) Genotypes

| Genotypes | Root Depth (cm) |
|---|---|
| 'Emerald Dwarf' | 28.9 |
| 'Tifdwarf' | 19.3 |
| 'Tifeagle' | 12.2 |

*Measurement of depth of deepest roots in 11.4 cm$^2$ column samples removed from replicate plots maintained under putting greens maintenance, with samples taken 30 months after planting. HOC was 0.125 April-October, 0.157 November-March. Means of four replications assessed October 2001.

Root Mass

A detailed, quantitative assessment was made of the root mass. 'Emerald Dwarf' has been found to have a comparatively greater root mass after 30 months, with a 525% greater total root mass than 'Tifeagle,' and 108.3% greater total root mass than 'Tifdwarf.' This is shown by Table 8 below. As shown by the table, 'Emerald Dwarf' had a significantly higher root mass at each sample depth.

TABLE 8

Root Mass After 30 Months* Comparisons Among Three Bermudagrass (*Cynodon* spp.) Genotypes

| Genotypes | 0-3" (mg) | 3-6" (mg) | >6" (mg) | Total (mg) |
|---|---|---|---|---|
| 'Emerald Dwarf' | 241 | 153 | 131 | 525 |
| 'Tifdwarf' | 154 | 83 | 15 | 252 |
| 'Tifeagle' | 72 | 12 | 0 | 84 |

*Weight of roots at three different depths in 11.4 cm$^2$ column samples removed from replicate plots maintained under putting greens maintenance, with samples taken 30 months after planting. HOC was 0.125 April-October, 0.157 November-March. Means of four replications assessed October 2001.

Rhizome Production

Figure 13:
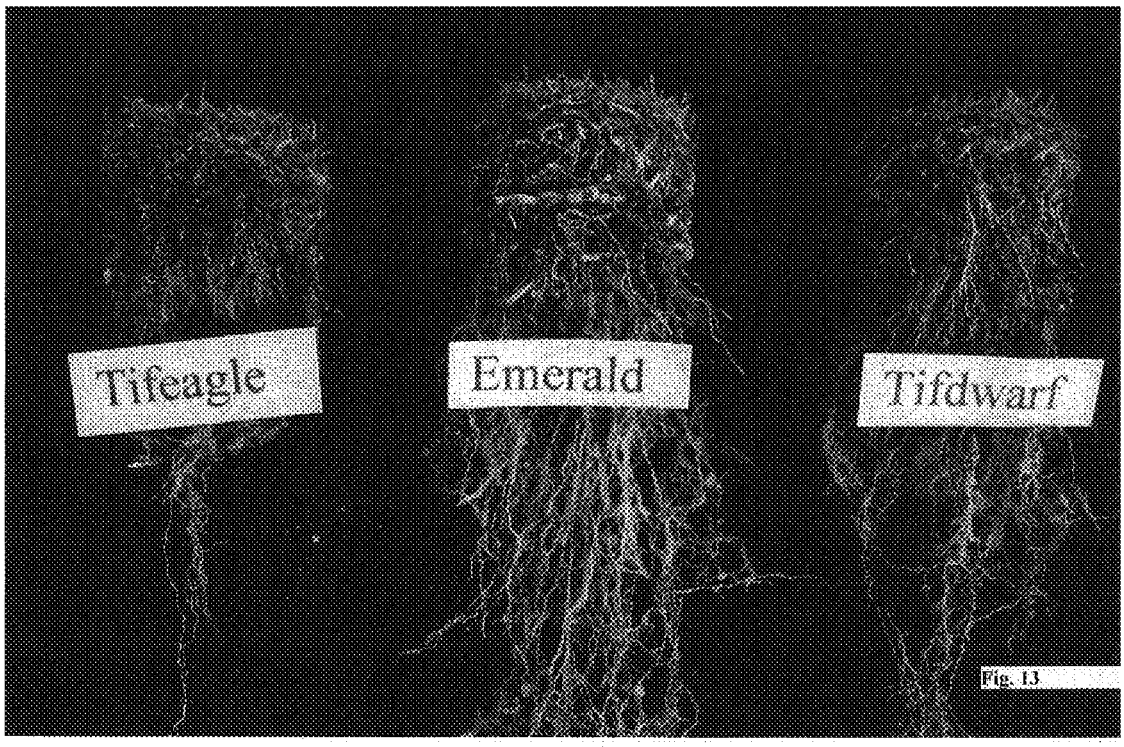
FIG. 13 is a photograph of comparative profiles of 'Tifeagle,' 'Emerald Dwarf,' and 'Tifdwarf,' taken 30 months after planting, illustrating rhizome formation.
Figure 14:
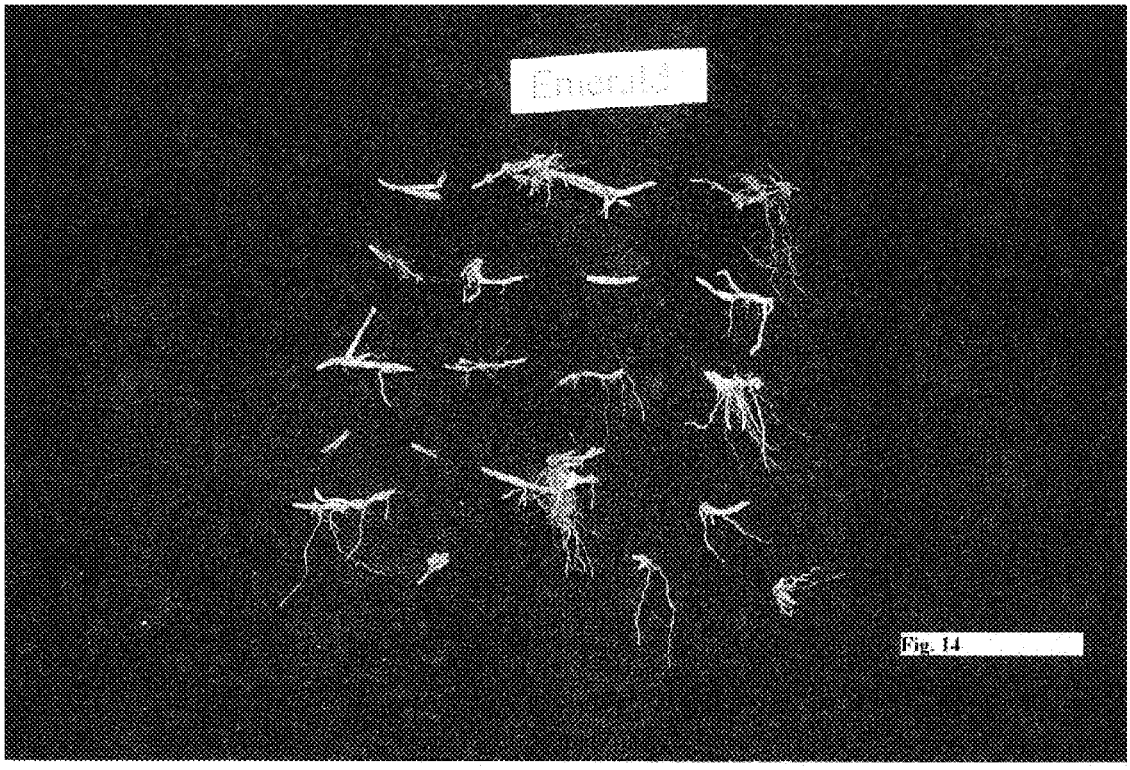
FIG. 14–15 are photographs of rhizomes collected from samples of 'Emerald Dwarf' and 'Tifdwarf'.
Figure 15:
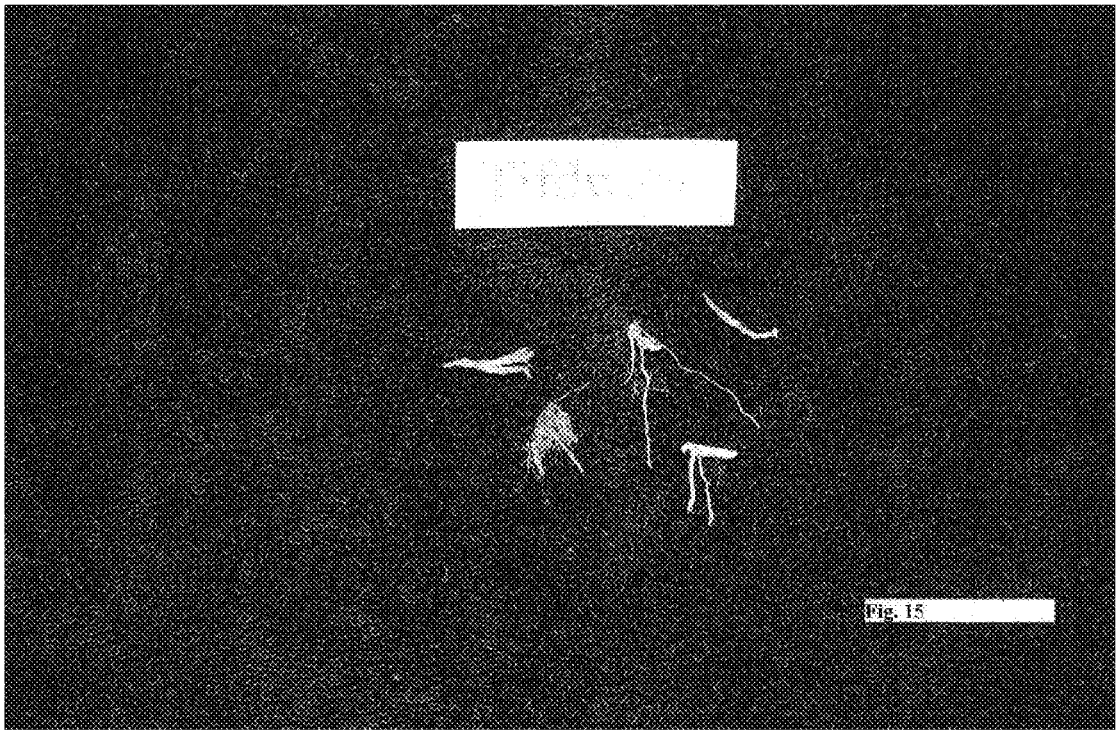

A detailed, quantitative assessment was made of the rhizome production of three Bermudagrass cultivars under putting green maintenance. 'Emerald Dwarf' has been found to have a comparatively greater rhizome production after 30 months, with a 57.9% greater rhizome production than 'Tifdwarf.' 'Tifeagle' showed not measurable rhizome production in that time period. This is shown by Table 9 below. FIGS. 13–15 illustrate comparative rhizome production of 'Emerald Dwarf' and 'Tifdwarf' after 30 months at putting greens height (0.125"–0.187").

TABLE 9

Rhizome Production After 30 Months* Comparisons Among Three Bermudagrass (*Cynodon* spp.) Genotypes

| Genotypes | Rhizome Production (mg) |
|---|---|
| 'Emerald Dwarf' | 240 |
| 'Tifdwarf' | 152 |
| 'Tifeagle' | — |

*Weight of viable lateral stems growing 1 cm or deeper below the surface in 11.4 cm$^2$ column samples removed from replicate plots maintained under putting greens maintenance, with samples taken 30 months after planting. HOC was 0.125 April-October, 0.157 November-March. Means of four replications assessed October 2001.

Depth of Deepest Rhizomes

Figure 16:
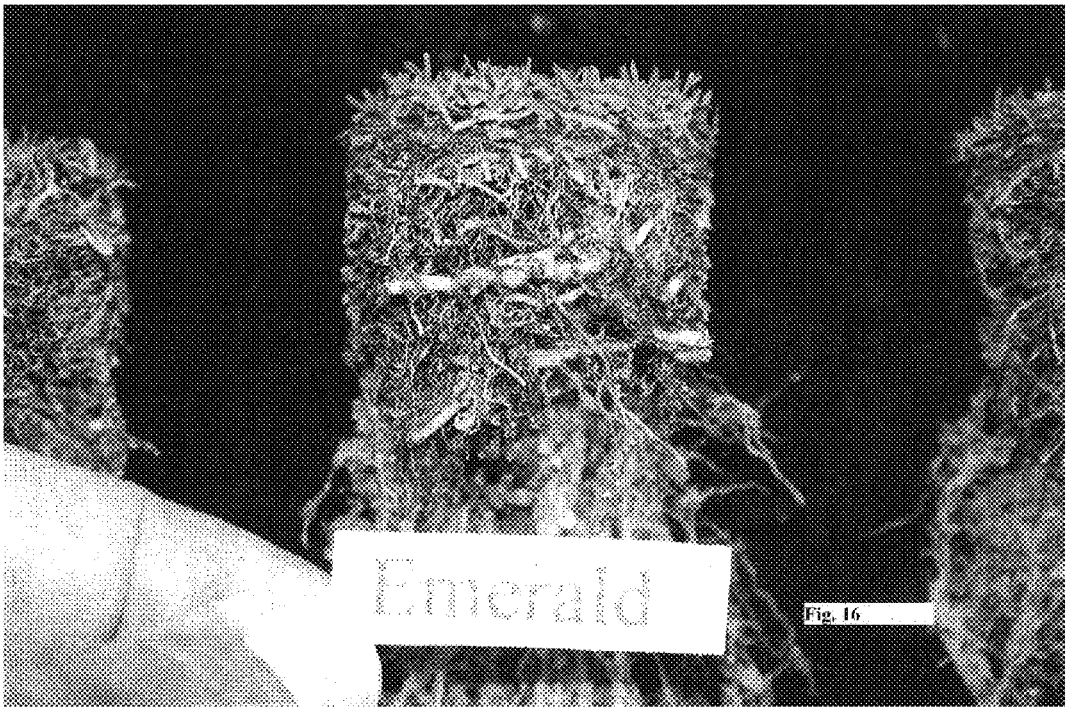
FIGS. 16–18 are close-up photographs of sample columns of 'Tifeagle,' 'Tifdwarf,' and 'Emerald Dwarf' illustrating the location of rhizomes in the columns.
Figure 17:
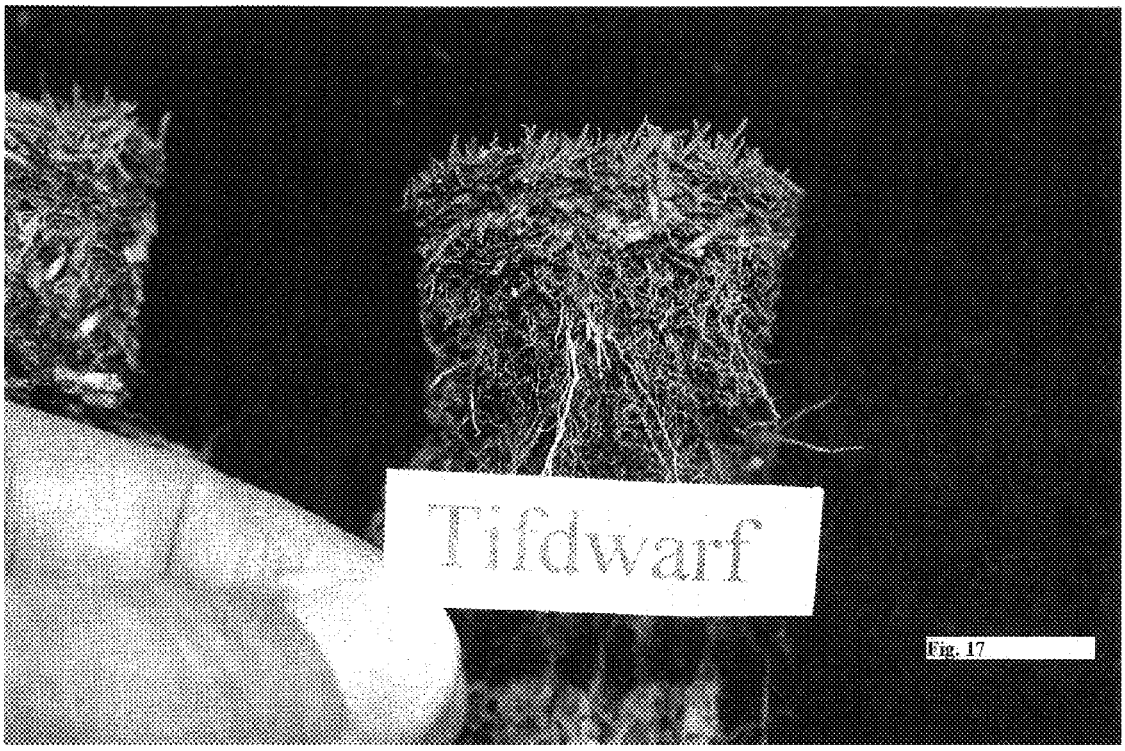
Figure 18:
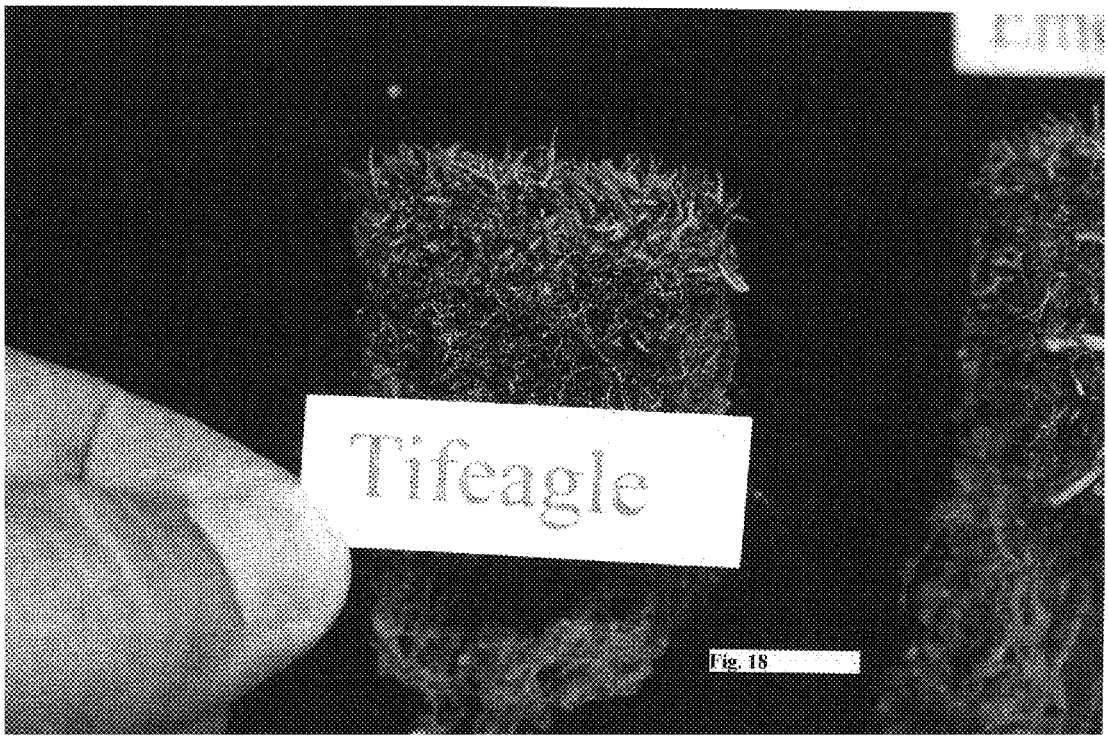

A detailed, quantitative assessment was made of the depth if the deepest rhizomes of three cultivars under putting green maintenance. 'Emerald Dwarf' has been found to have a comparatively greater deepest rhizome depth after 30 months, with a 126.7% greater depth than 'Tifdwarf.' 'Tifeagle' showed no measurable rhizome production in that time period. This is shown by Table 10 below. FIGS. 16–18 illustrate comparative rhizome depths of the three cultivars after 30 months at putting greens height (0.125–0.187").

TABLE 10

Depth of Deepest Rhizomes After 30 Months* Comparisons Among Three Bermudagrass (*Cynodon* spp.) Genotypes

| Genotypes | Depth (cm) |
|---|---|
| 'Emerald Dwarf' | 3.4 |
| 'Tifdwarf' | 1.5 |
| 'Tifeagle' | — |

*Depth of deepest viable lateral stems as measured from soil surface in 11.4 cm$^2$ column samples removed from replicate plots maintained under putting greens maintenance, with samples taken 30 months after planting. HOC was 0.125 April-October, 0.157 November-March. Means of four replications assessed October 2001.

Deep Rhizome Development

Compared to the other known greens cultivars, and particularly when compared to ultradwarf cultivars, the 'Emerald Dwarf' cultivar produces substantially greater rhizomes. Some of the benefits of this growth habit for application on a putting green are:

1. 'Emerald Dwarf' allows for better water infiltration because the lateral stems are not stacked on the surface to form an organic barrier but are distributed throughout the top inch or more of the profile.
2. 'Emerald Dwarf' is much less prone to scalping because the stems are down in the soil out of reach of the mower. This allows for architectural features such as more sever slopes that would create difficulties for more stoloniferous cultivars.
3. The surface created is more inherently firm, which is a major component of putting surface ball-roll speed.
4. 'Emerald Dwarf' has a reduced topdressing requirement because there is less need for dilution of the stem biomass.
5. 'Emerald Dwarf' has a reduced aerification requirement because there is less organic matter creation due to less stem biomass at the surface.
6. 'Emerald Dwarf' can withstand infrequent, deep verticutting because the mower is supported on a firm surface as opposed to a bed of lateral stems as is the case with a highly stoloniferous grass.
7. Because there is less thatch creation due to the lesser stem accumulation, the grass can be managed with higher nitrogen levels, resulting in more vigor, better recuperative potential, dark-green turf color described by the R.H.S. Color Chart as R.H.S. 138A, medium light green.
8. The turf created is more receptive to overseeding with cool season grasses, including large-seeded species such as ryegrass.

Deep Rooting

Compared to the other known greens cultivars, and particularly when compared to ultradwarf cultivars, the 'Emerald Dwarf' cultivar produces substantially deeper roots. Some of the benefits of this growth habit for application on a putting green are:

1. 'Emerald Dwarf' has better water uptake throughout the soil profile. This allows for less frequent watering, particularly on a perched water table design rootzone (such as USGA Specification green).
2. 'Emerald Dwarf' has better nutrient uptake throughout the rootzone profile. This makes granular fertilizer applications more effective, reducing or eliminating the need for foliar fertilizer applications.
3. 'Emerald Dwarf' will perform well in coarse sand rootzones (such as USGA Specification green) because of the ability to draw moisture from deep within the profile.
4. 'Emerald Dwarf' can better withstand poor irrigation water quality because of the ability to water deeply and infrequently which flushes the salts down through the rootzone.
5. 'Emerald Dwarf' is less prone to moisture stress, "hot spots", etc. because of the deeper rooting. This allows for architectural features such as high mounds and more severe slopes that would be difficult to manage with more shallow rooted cultivars.

Overseeding and Transition

The University of California at Riverside Coachella Valley Agricultural Research Station evaluated warm-season turfgrasses for putting green use in the Coachella Valley. The grasses were established with stolons in early April 2001, to a sand based putting green plot. The specifications for the construction of the simulated putting green followed those commonly used in recently constructed golf courses in the Coachella Valley. There were three replications of each grass chosen for the study and the field study was arranged in a randomized block design. The site was managed through grow-in as is commonly performed in the local area. The specific management practiced was as follows:

*Mowing height.*—0.125 inch. The mowing height was reduced slowly following establishment, over a 30-day period, to the desired mowing height. The height was kept constant throughout the calendar year, until overseeding.

*Frequency.*—Mowing was performed 6–7 times per week, skipping Sunday if 6 times per week.

*Mowing pattern.*—The research area was mowed north and south (length of grass plots) until plots filled together, than the plot area was mowed at various directions (alter direction) to eliminate the development of grain.

*Clippings.*—Removed throughout study.

*Turf grain control.*—An appropriate groomer on the mower was used as needed to prevent turf grain formation. Particular attention to grain control was paid when the grass was growing vigorously during the late spring, summer, and early autumn.

*Fertilization.*—The study area was fertilized at the annual rate of 5 lbs N/1000 sq ft; 1.6 lbs P; and 2.5 lbs K using a 15-5-8 fertilizer. The rate of 0.5 lbs N/100 sq ft was applied in mid-March to early April as a spring bump, then 0.3 lbs N/1000 sq ft per 3 weeks. In February 2003, the three-week application was increased in rate to 0.4 lbs N/1000 sq ft. The fertilizer was applied in two directions at each application time.

*Cultivation-verticutting.*—During spring, summer and early autumn (May 1- October) light verticutting was performed every 3 weeks. Attention was given to prevent damage to turf if the grass was not growing vigorously.

*Topdressing.*—A light sand topdressing was applied 1 week after vertical mowing, May-October.

*Aerification.*—A ⅜-inch hollow tine aerifier was used to remove cores in early October 2002 in association with the overseeding operation.

*Overseed process.*—Overseeding was done on Oct. 10, 2002. It was preceded with a vigorous vertical mowing with the organic matter removed. The green was aerified, cores allowed to dry and then shattered. Sand from the cores was dragged and surface material removed from the green. The green was overseeded with a mix of perennial ryegrass and rough stalk bluegrass. CBSII blend of perennial ryegrass ('Brightstar II' at 33.12%, 'Quickstart' at 32.73%, and 'Charger II' at 32.71%) was overseeded at the rate of 20 lbs/1000 sq ft. 'Winterplay' *Poa trivialis* was overseeded at the rate of 8 lbs/1000 sq ft and followed by weekly overseeding at the rate of 1 lb for two weeks (10 lbs seed/1000 sq ft total). A sand top-dressing followed the primary overseeding operation. The overseeded grasses were germinated with frequent irrigation until seedlings were established.

*Data collected.*—Visual recordings of turf performance were collected, usually every two weeks, throughout the study period. Grass establishment, quality, color, and plot uniformity were rated on a 1–9 scale with 9 representing the highest level of each characteristic and 1 representing the lowest or absence of the characteristic. Percentage of warm-season grass was recorded on a 0–100% scale. The data were grouped into time periods of similar performance based on maturity and time of year so the results are presented an analysis performed on data from those time periods. An analysis of variance was performed on collected results from the randomized complete block designed study. Repeated measures analysis was used with dates treated as the repeated factor within the time period of analysis. Significant difference was determined by Fishers Protected LSD at the 0.05 level of probability. All grasses completely covered the plots by September, following the April establishment. The study was overseeded in October 2002. Color and quality of the overseeded swards were evaluated for play season (November-May) and for the transition season of June-July when the cool-season grasses died out and the warm-season achieved cover and dominated the sward. The results, shown in Table 11 below, indicate that 'Emerald Dwarf' has comparatively better color and higher quality than the measured ultradwarf turfgrass.

TABLE 11

Overseeding Color and Quality* Comparisons Between 'Emerald Dwarf' and Ultradwarf Bermudagrasses

| Genotypes | November 2002-May 2003 Color | November 2002-May 2003 Quality | June 2003-July 2003 Color | June 2003-July 2003 Quality |
|---|---|---|---|---|
| 'Emerald Dwarf' | 6.6 | 6.5 | 6.6 | 6.2 |
| Ultradwarf Bermudagrasses** | 6.5 | 6.4 | 6.5 | 4.8 |

*Color and quality of overseeded putting greens grasses November 2002 through July 2003. Ratings: 1 = poor quality/light color; 9 = excellent quality/dark green color.
**Composite score of ratings of four ultradwarf Bermudagrasses ('Champion,' 'Floradwarf,' 'Miniverde,' 'Tifeagle'), performed October 2003 at University of California Riverside Coachella Valley Agricultural Research Station Uniformity ratings, which account for the way the warm-season and cool-season overseeded grass interacted in the study, were also evaluated and the results are presented in Table 12, and the percentage of warm-season grass during the transition period in Table 12. It can be observed that the uniformity ratings do not differ much during April-May when the cool-season overseeded mix was present. The results, shown in Tables 12–13 below, indicate that 'Emerald Dwarf' has better uniformity and a higher percentage of Bermudagrass during the transition period than the ultradwarf grasses.

TABLE 12

Uniformity During Transition* Comparisons Between 'Emerald Dwarf' and Ultradwarf Bermudagrasses

| Genotypes | April-May 2003 | June-July 2003 | August 2003 |
|---|---|---|---|
| 'Emerald Dwarf' | 6.4 | 6.6 | 6.7 |
| Ultradwarf Bermudagrasses** | 6.4 | 4.9 | 5.4 |

*Uniformity of putting green turfs leading up to and during transition of overseeded putting green grasses, April 2003 through July 2003.. Ratings: 1 = non-uniform; 9 = uniform surface.
**Composite score of ratings of four ultradwarf Bermudagrasses ('Champion,' 'Floradwarf,' 'Miniverde,' 'Tifeagle'), performed October 2003 at University of California Riverside Coachella Valley Agricultural Research Station

TABLE 13

Percentage of Bermudagrass* Comparisons Between 'Emerald Dwarf' and Ultradwarf Bermudagrasses

| Genotypes | April 2003 | June 2003 | July 2003 | August 2003 |
|---|---|---|---|---|
| 'Emerald Dwarf' | 51.7 | 70.0 | 83.3 | 90.0 |
| Ultradwarf Bermudagrasses** | 43.3 | 42.9 | 67.5 | 86.7 |

Figure 20:
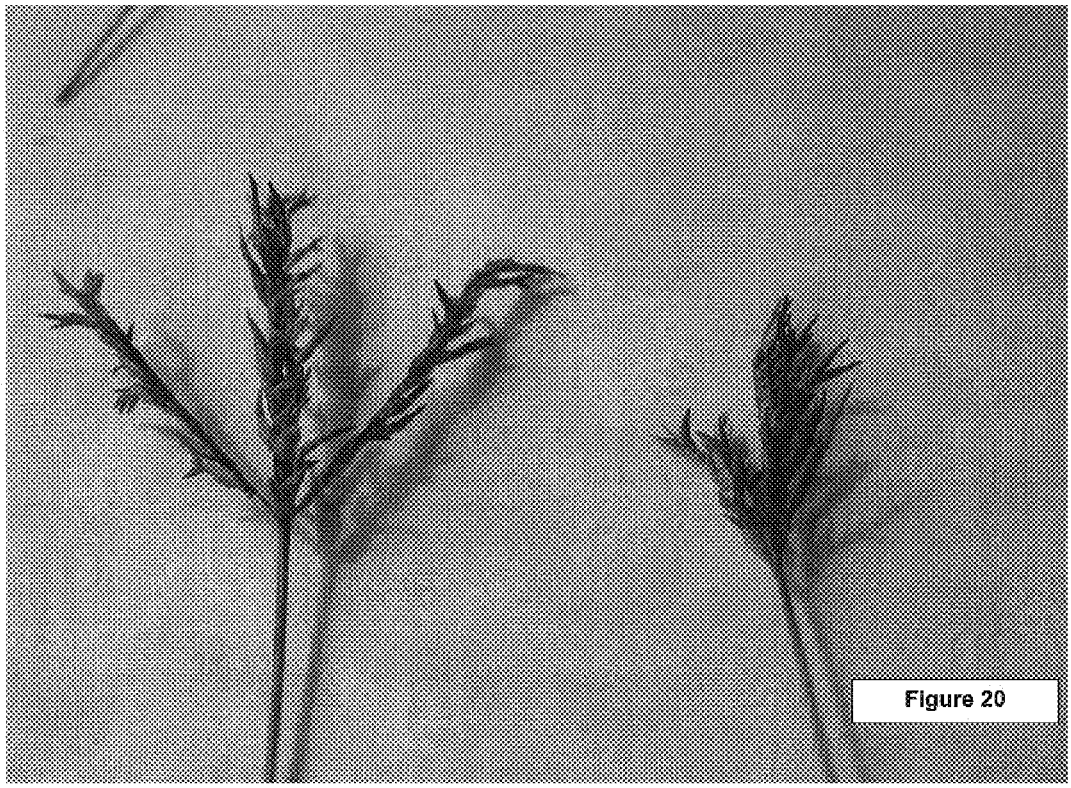
FIG. 20 is a close-up photograph of 'Emerald Dwarf' illustrating small vegetative shoots produced by the seeds while they are attached to the seedhead.

*Percent coverage of Bermudagrass leading up to and during transition of overseeded putting greens grasses April 2003 through August 2003.
**Composite score of ratings of four ultradwarf Bermudagrasses ('Champion,' 'Floradwarf,' 'Miniverde,' 'Tifeagle'), performed October 2003 at University of California Riverside Coachella Valley Agricultural Research Station Detailed Characteristics A detailed description of the new and distinct genotype of hybrid Bermudagrass named 'Emerald Dwarf' includes:

1. a unique relative ratio of rhizome and stolon production, with a ratio of about 60% rhizomes to 40% stolons;
2. a unique rooting depth, on the order of 28–29 cm after 30 months, with rhizomes growing deeply in the profile and distributed throughout the first 1" of the profile, rather than being stacked near the surface;
3. a shoot density higher than 'Tifdwarf,' but lower than high-density ultradwarfs, that produces a uniform, high-quality turf surface with relatively little thatch accumulation compared to high-density cultivars, where the shoot density is maintained in the fall;
4. the internode length of stolons is on the order of 14–15 mm;
5. the leaf width is on the order of 1.3 mm under very close mowing;
6. a total root mass on the order of 525 mg after 30 months,
7. the leaves are folded in the bud shoot;
8. the leaf blades are flattened to v-shaped in cross-section, keeled, and gradually tapering to an acute point;
9. the ligule at the junction of the leaf blade and leaf sheath is a fringe-of-hairs;
10. there is no auricle present;
11. the collar on the opposite side from the ligule is a continuous, narrow band;
12. the lateral stems, both stolons and rhizomes, branch profusely at the nodes;

13. each node-cluster produces three leaves;

14. the roots originate from nodes and are fine, fibrous, and dense;

15. the unmowed shoot growth height is on the order of 2 inches (50 mm); and 16. the seeds produce small vegetative shoots while they are attached to the seedhead. (See FIG. 20).

These characteristics produce greens that:

1. keep better infiltration;
2. are not prone to scalping;
3. do not require a great deal of topdressing;
4. do not require extensive aerification;
5. do not require frequent watering;
6. can withstand infrequent, deep verticutting;
7. can be managed with higher nitrogen, resulting in more vigor, better recuperative growth;
8. will readily accept overseeding;
9. will perform well in coarse sand rootzones;
10. can withstand poor water quality; and
11. are less prone to stresses.

We claim:

1. A new and distinct Bermudagrass plant, substantially as herein shown and described, distinguished by greater rhizome development and rooting depth in conjunction with low surface stolon development, yet having shoot density sufficient to enable it to withstand mowing at very low putting green heights.

* * * * *